United States Patent [19]

Vetter et al.

[11] Patent Number: 4,774,772

[45] Date of Patent: Oct. 4, 1988

[54] APPARATUS FOR HANDLING SYRINGE BODIES

[75] Inventors: Helmut Vetter, Marienplatz 81, D-7980 Ravensburg; Peter Geprägs, Weingarten, both of Fed. Rep. of Germany

[73] Assignee: Helmut Vetter, Ravensburg, Fed. Rep. of Germany

[21] Appl. No.: 11,337

[22] Filed: Feb. 5, 1987

[30] Foreign Application Priority Data

Apr. 22, 1986 [DE] Fed. Rep. of Germany ....... 3613489

[51] Int. Cl.$^4$ ............................................. F26B 25/00
[52] U.S. Cl. ....................................... 34/105; 34/107; 34/39; 34/106; 211/69
[58] Field of Search ..................... 211/69; 34/104, 105, 34/106, 107, 39, 21

[56] References Cited

U.S. PATENT DOCUMENTS 2,748,495  6/1956  Murray ................................. 34/107
3,349,937 10/1967  Duff et al. ............................ 211/69

Primary Examiner—Henry A. Bennet
Attorney, Agent, or Firm—Herbert Dubno

[57] ABSTRACT

The apparatus for handling a finished syringe bodies comprises a planar supporting plate and a mounting plate provided with foot members attached with the supporting plate substantially parallel thereto by a plurality of spacing pieces. Both supporting plate and mounting plate have a plurality of receiving openings for the injection molding devices positioned pairwise coaxial to each other and a retaining plate is provided with holes coaxial to the receiving openings and connected detachably to the supporting plate on the side of the supporting plate facing away from the mounting plate. The boundaries of the holes in the retaining plate form an axial contacting surface for the injection molding devices placed in the receiving openings.

9 Claims, 5 Drawing Sheets

U.S. Patent  Oct. 4, 1988  Sheet 5 of 5  4,774,772
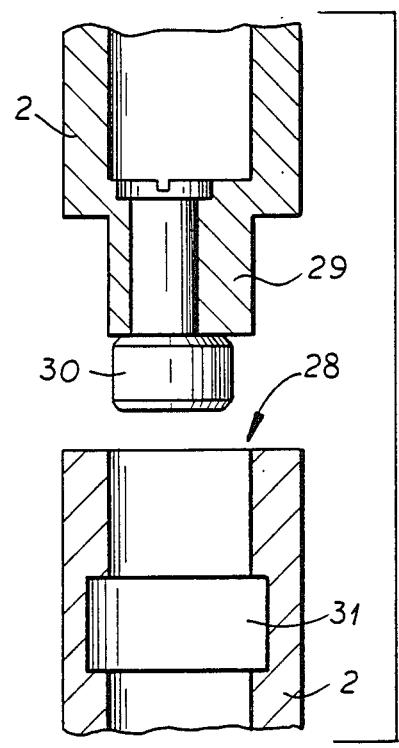
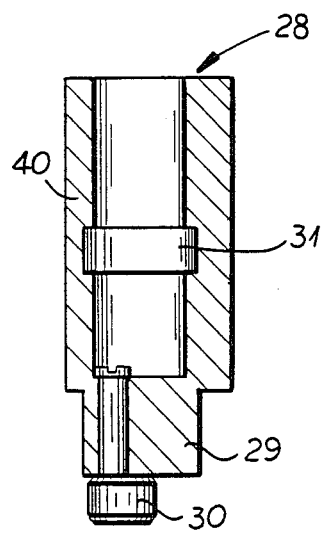
FIG.6
FIG.6A
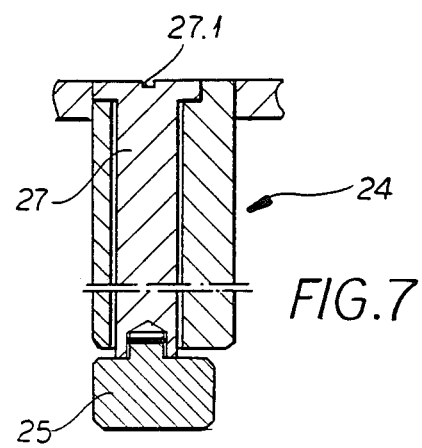
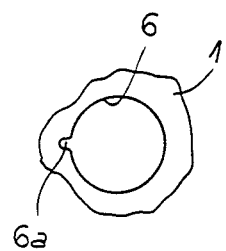
FIG.1A
FIG.7

APPARATUS FOR HANDLING SYRINGE BODIES

FIELD OF THE INVENTION

Our present invention relates to an apparatus for handling syringe bodies and like injection-molded or glass tubular articles, e.g. for deburring, cleaning, sterilization and other procedures up to final labelling.

BACKGROUND OF THE INVENTION

In the course of the individual processing steps involved in the fabrication of syringe bodies and like injection molded articles, e.g. from the end of cleaning up to the final labelling, because of poor structure stability, the syringe bodies are generally treated in randomly distributed or piled masses. This means that the syringes must be oriented again for each new process step, i.e. they must be brought into a predetermined positioning or orientation for further processing. Particularly in mechanical processing this takes an exceptional amount of work and requires additional mechanical devices to perform this sorting or orientation.

There are already known auxiliary devices, e.g. bucket or cup chains, suspension rails or the like, with which the finished syringe bodies can be transported and further processed. However these devices, which are comparatively expensive and troublesome, can lead to damage to the syringes to be processed. Also such devices are susceptable to breakdown and only adjustable to changing process conditions with great difficulty or not at all.

OBJECTS OF THE INVENTION

It is an object of our invention to provide an improved apparatus for handling furnished syringe bodies which will obviate the drawbacks of earlier syringe-handling systems.

It is also an object of our invention to provide an improved apparatus for handling furnished syringe bodies by which the furnished syringe bodies are made available for the individual process steps in an ordered and oriented arrangement which is also constructed and arranged so that all required operating steps can be taken without removal or resorting of the individual furnished syringe bodies.

SUMMARY OF THE INVENTION

These objects and others which will become more readily apparent hereinafter are attained in accordance with our invention in an apparatus for handling furnished syringe bodies.

According to our invention the apparatus for handling an furnished syringe bodies comprises a planar supporting plate, an mounting plate provided with foot members and connected with the supporting plate, the mounting plate being positioned substantially parallel to the supporting plate by a plurality of spacing pieces. Both supporting plate and mounting plate have a plurality of receiving openings for the furnished syringe bodies positioned pairwise coaxial to each other (i.e. in axial registry) and a retaining plate is provided with holes coaxial with the receiving openings and is connected detachably to the supporting plate on the side of the supporting plate facing away from the mounting plate. The boundaries of the holes in the retaining plate form axial contacting surfaces for the flanges of the furnished syringe bodies placed in the receiving openings.

We are thus able to mount the furnished syringe bodies held in the device of the invention in the individual processing stations in a plurality of arrangements and orientations, even upside down, so that particularly automatic processes can run reasonably and without allowing the syringe bodies to fall out of the apparatus. However the retaining plate because of the holes provided in it allows free access to the interior of the injection molding cylinder and/or the insertion of the plungers in the syringe bodies.

The arrangement and number of the receiving openings in the supporting and/or mounting plate can be correspondingly adjusted to fit the structure of the individual processing station. Thus rows of openings can be provided $6 \times 6$, $8 \times 8$ or $12 \times 12$ for example to allow the processing in two, four or six position processing stations.

The receiving openings advantageously are circular holes. Each of the receiving openings in the supporting plate can have a size so that it can receive an furnished syringe bodies with a bypass or can have an additional recess clearing the bypass.

To provide a saving of space the receiving openings are positioned at the insection points of two sets of parallel straight lines (through the centers of the openings) positioned equidistant from each other. The sets of straight lines intersect each other at an angle of 60° and the straight lines of one of the sets are parallel to a longitudinal side of the supporting and/or mounting plate. As a result an arrangement is provided in which the receiving openings are at the corners of equilateral triangles. Because of that there is an equal inside spacing between the receiving openings which is so dimensioned that the inserted furnished syringe bodies can be removed rowwise with a fork shaped device.

In one embodiment of our invention the retaining plate is provided on two opposing edges with a U-shape profile extending in the longitudinal direction of the edges, wherein both of the grooves formed by the U-shape profile are directed to each other and form guiding recesses for the edges of the supporting plate. Thus the retaining plate can be attached easily by pushing the supporting plate into these recesses and also can be easily, if necessarily automatically, pulled off again for removal of the furnished syringe bodies. To attain exact alignment of the receiving openings in the retaining plate to those in the supporting plate in a particularly simple way the free leg of the U-shape profile can have a projection protruding in the plane of that leg at its free end which forms a contacting surface for one of the spacing pieces with concentric alignment of the receiving openings in the retaining plate and the supporting plate.

It is necessary to fix the retaining plate in its position for additional manipulation of the apparatus it is of advantage to provide in the free leg of the U shape profile a retaining pin or detent which can protest into the groove and which with its front end can engage in a locking recess of the supporting plate with concentric alignment of the receiving openings in the retaining plate and the supporting plate.

Advantageously the spacing piece is formed by a plurality of cylindrical pipe, tube or sleeve sections and with the foot members in one piece. Also it is advantageously possible to provide a retaining plate carrying a plurality of alignment pins projecting perpendicularly from its surface which are positioned with the retaining plate oriented toward the supporting plate coaxial to the spacing pieces, the cylindrical space in each of the spacing pieces forming a receiving member for one of the alignment pins.

At least one of the alignment pins carries on a free end thereof an eccentric mounted rotatably eccentric to the axis of its alignment pin which is positioned inside the extended generated surfaces of the alignment pin according to rotary position thereof and can be rotated to project beyond it radially and engage in an inner circular groove provided in the spacing piece. Thus the retaining piece must not be pushed transverse to the receiving openings, but can be mounted from above which simplifies the assembly process.

An additional embodiment of our invention is particularly characterized by spacing pieces divided transverse to their longitudinal axis and releasably attached to each other by a socket sleeve and a socket foot insertable in the socket sleeve, the end of the socket foot carrying an eccentric disk mounted eccentrically on the axis of the socket foot which is found in the extended generated surfaces of the socket foot depending on the rotational position of the eccentric or projects over the socket foot radially and engages in an interior groove provided in the spacing piece. This makes it possible to divide the apparatus at the spacing pieces, whereby at the separating points of the spacing pieces an adapter member is insertable whose one end is provided with one of the socket sleeves and whose other end is provided with one of the socket feet. In this way the apparatus can be adjust to fit different length furnished syringe bodies to be processsed by insertion of different length adapters.

It is also advantageous when a plurality of positioning devices in the form of grooves, toothed bars or recesses which are provided on the supporting and/or mounting plates for automatic manipulation.

In particularly advantageous structure of our invention, the foot members are provided with axially extending guiding surfaces for a closure member plate movable toward the mounting plate and mountable in a parallel orientation on the mounting plate, the closure member plate having a plurality of mounting sockets for the closure members which are positioned coaxial to the receiving openings in the mounting plate. Thus it is possible to close all the furnished syringe bodies in an operation by the closure members mounted in the mounting sockets, wherein the exact fitting feed of the closure members is guaranteed on the one hand by the mounting plate aligning the furnished syringe bodies and on the other hand by the guiding of the closure member plate along these guide surfaces. In a particularly simple way the guiding surfaces are cylindrical inner surfaces of the pipe sections forming the foot members in which a plurality of guide pins protruding vertically from the closure member plate are guided axially slidably. To make the insertion of the guide pins in the cylindrical space in the foot members easier, the front ends of the guide pins have a truncated cone shape.

To hold the closure member plate with spacing from the mounting plate in the process step preceeding closure of the finished syringe bodies a coil spring is mounted coaxial to each of the guide pins which is connected with one end thereof on the closure member plate and whose other end presses on the front end of the foot member. To close the finished syringe bodies then the closure member plate can be pressed against the force of the coil spring for example by a press plate directed toward the mounting plate.

The closure members can be reliably prevented from falling out of the mounting sockets in spite of the existing manufacturing tolerances by providing the mounting sockets with a circular groove on the inner surface thereof surrounding the closure member engaged therewith in which the closure member engages with radially protruding deformable naplike projections.

This ensures that the closure members after being engaged with the finished syringe bodies can be pulled from the mounting sockets.

To ensure contacts of all parts of the apparatus with sterilizing steam the supporting plate and/or the mounting plate and/or the retaining plate and/or the closure member plate are each provided with a plurality of flow passages.

In regard to the process steps occuring at high and/or low temperatures such as sterilization or freeze drying, supporting, adjustable, retaining and closure member plates and the spacing piece and the foot members can be made from a material which is nondeformable in a temperature range from $-100°$ C. to $350°$ C., particularly from stainless steel.

BRIEF DESCRIPTION OF THE DRAWING

The above and other objects, features and advantages of our invention will become more readily apparent from the following description, reference being made to the accompanying highly diagrammatic drawing in which:

FIG. 1A is a fragmentary plan view of the top plate thereof in another embodiment;

FIG. 6 is a side sectional view of a part of the apparatus of FIG. 5 shown in the dot-dash circle VI of FIG. 5;

FIG. 6a is a side sectional view of an adapter member of the apparatus of FIG. 5; and FIG. 7 is a side sectional view of a part of the apparatus of FIG. 5 shown in the dot-dash circle VII of FIG. 5.

SPECIFIC DESCRIPTION

Figure 1:
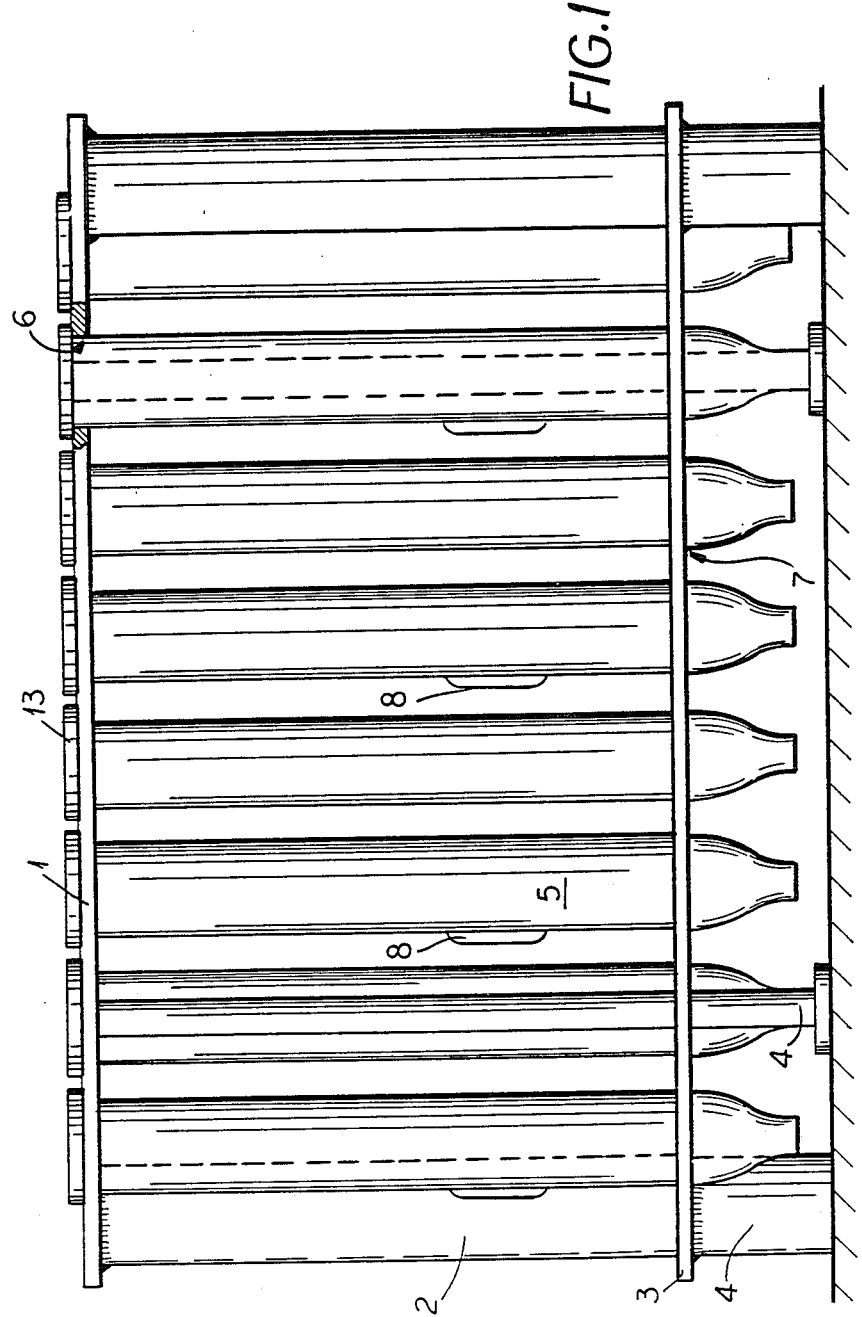
FIG. 1 is a side elevational view of an apparatus for handling finished syringe bodies.

The apparatuses shown in the drawing are for handling a plurality of furnished injection-molded plastic or even glass syringe bodies 5, particularly in further processing and treatment in connection with cleaning and up to its final labelling.

The apparatus shown in FIG. 1 comprises in detail a supporting plate 1 which is connected with an mounting plate 3 mounted parallel to it by a plurality of spacing pieces 2. Further the mounting plate 3 has foot members 4 which provide the planar mounting of the apparatus. Each spacing piece 2 is formed with foot members 4 in one piece and a cylindrical pipe section which extends through an opening in the mounting plate 3. These pipe sections can be welded with the supporting and mounting plates 1, 3.

The supporting plate 1 and the mounting plate 3 are both provided with receiving openings 6, 7 pairwise coaxial to each other for an furnished syringe bodies 5. These receiving openings 6, 7 are formed by circular holes and the receiving openings 6 in the supporting plate 1 have such a size that they may receive also an furnished syringe bodies 5 provided with a bypass 8.

Alternatively (FIG. 1A) recesses 6a can be provided to clear the bypass.

Figure 2:
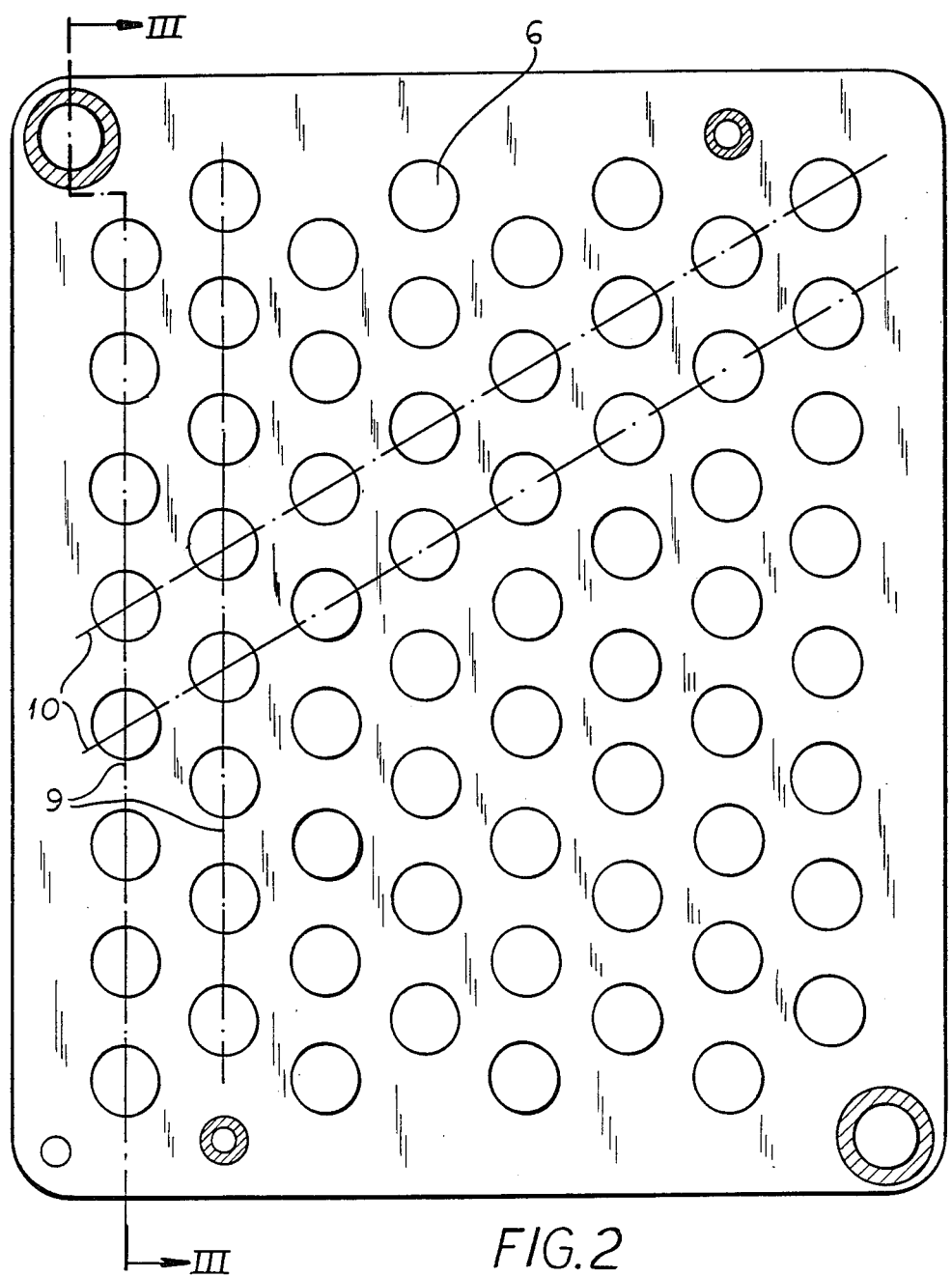
FIG. 2 is a top plan view of the apparatus according to FIG. 1.
Figure 3:
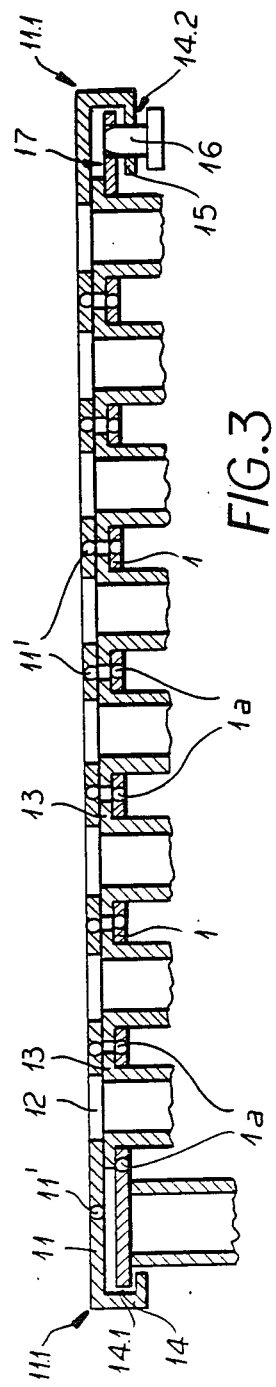
FIG. 3 is a partial longitudinal cross sectional view through the apparatus according to FIG. 2 taken along the section line III—III thereof with the retaining plate mounted thereon.

As seen in FIG. 2 the receiving openings 6,7 are positioned at the intersection points of two sets of parallel straight lines 9,10 positioned equidistant from each other whose straight lines intersect each other at an angle of 60°. One of each of the sets of straight lines 9 runs also parallel to the longitudinal side of the supporting and/or mounting plates 1,3.

The furnished syringe bodies 5 put in the apparatus are held by a retaining plate 11 which is connected detachably to the supporting plate 1 on its side facing away from the mounting plate 3. The retaining plate 11 is also provided with holes 12 which are positioned concentric to the receiving openings 6, 7, whereby the interior of the injection molding cylinder 5 remains accessible also with the retaining plate 11 mounted. The size of these holes 12 is chosen so that their boundaries form an axial contacting surface or stop for the flanges 13 furnished syringe bodies 5 mounted in the apparatus. As a result also the devices 5 are held in their axial position by the radially projecting circular flange 13 at their cylinder ends which engages between the supporting plate 1 and the retaining plate 3.

The retaining plate 11 is provided on both of two opposing edges 11.1 with a U-shape profile extending in the longitudinal direction of these edges 11.1, whereby it may be pushed on the supporting plate 1 in a particularly simple way. Moreover the grooves 14.1 formed by the U-shape profile point to each other and form guiding receiving openings for the edge of the supporting plate 1.

To be able to fix the position of the retaining plate 11 in its sliding direction, also in the longitudinal direction of the U-shape profile, the free leg 14.2 of the U-shape profile 14 has a projection 15 at its free end protruding into the plane of the leg 14.2 which forms a contacting surface for one of the spacing piece 2.

The position of the projection 15 is so selected that a concentric alignment of the receiving openings 6 and holes 12 in the retaining plate 11 and the supporting plate 1 results. To hold the retaining plate 11 in this position unshiftably a retaining pin 16 (detent) which can engage in the groove 14.1 is mounted which projects with its front end into a locking receptacle 17 of the supporting plate 1 with concentric alignment of the receiving openings 6 and holes 12 in the retaining plate and the supporting plate 1.

Figure 5:
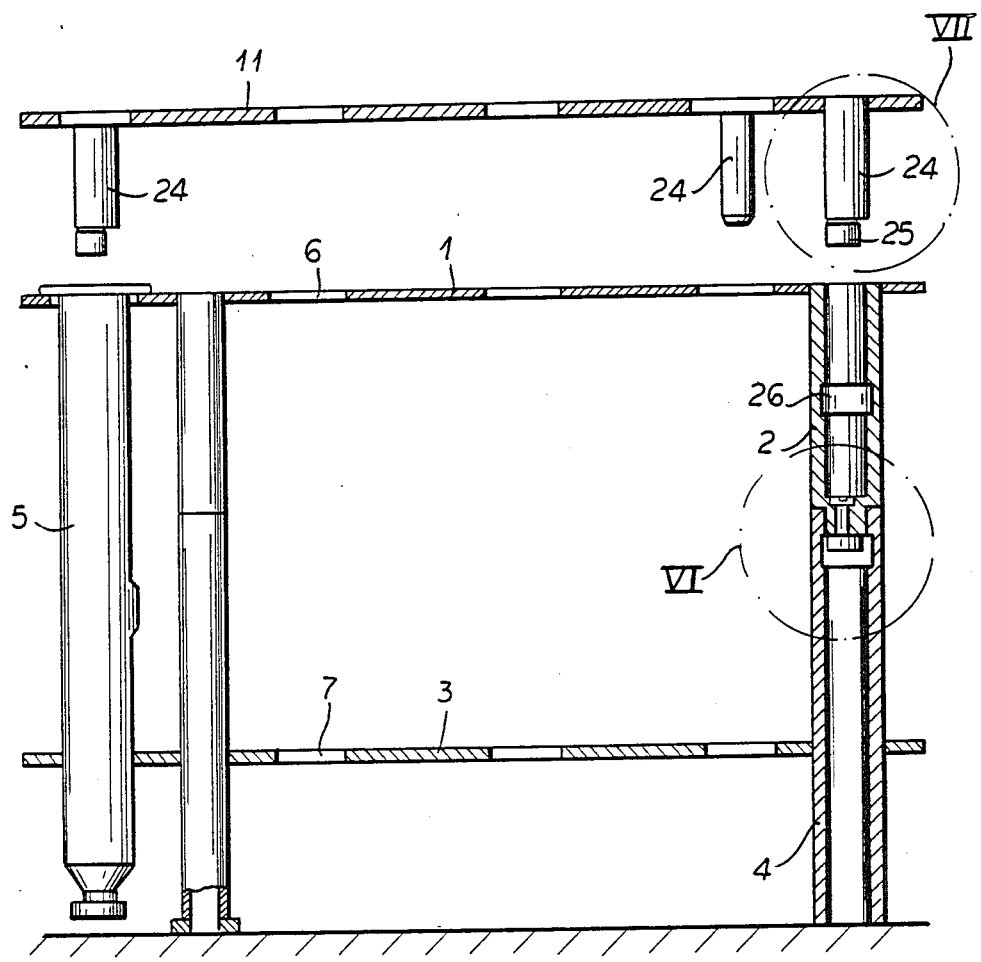
FIG. 5 is a partially sectional view of another embodiment of an apparatus for handling finished syringe bodies corresponding to FIG. 3.

In the embodiment shown in FIG. 5 the retaining plate 11 is mountable in the axial direction for receipt of the furnished syringe bodies 5 on the supporting plate 1. Moreover the retaining plate 11 carries projecting alignment pins 24 perpendicular to their surface which are arranged coaxial to the spacing pieces 2 with the retaining plate 11 positioned opposite the supporting plate 1. Each cylindrical hollow space of the spacing pieces 2 forms a receptacle for a alignment pin 24. At least one of the alignment pins 24 carries at its free end an eccentric disk 25 mounted rotatably eccentrically to the axis of the alignment pin 24 which according to its rotary position is positioned inside the extended generated surfaces of the alignment pin 24 or projects radially beyond it and engages thus in an inner circular groove 26 provided in the spacing piece 2.

As appears in detail from FIG. 7 the eccentric disk 25 is connected at the lower end of a rotatably mounted bolt 27 which is operable by a screwdriver inserted into a slot 27.1 or the like.

As seen from FIG. 5 the spacing pieces 2 are divided transverse to their axis and are attached with each other detachably by a socket sleeve 28 and a socket foot 29 insertable into it. The socket foot 29 carries at one end an eccentric disk 30 mounted eccentrically on its axis which depending on its rotational position inside the extended generated surfaces of the socket foot 29 or radially protrudes beyond it and thus engages in an interior groove 31 provided in the interior of the socket sleeve 28. Thus it is possible at the separating point of the spacing pieces 2 formed by the socket sleeve 28 and the socket foot 29 to insert an adapter member 40 shown in FIG. 6a whose one end likewise is provided with a socket sleeve 28 and whose other end is provided with a socket foot 29. By selection of such an adapter member 40 of suitable length the possibility exists then to choose the spacing between the supporting plate 1 and the mounting plate 3 to correspond to the length of the inserted furnished syringe bodies 5.

For the positioning or additional travel of the apparatus in an automatically operating plant positioning devices in the form of grooves 11a, toothed strips or openings can be provided in the supporting and/or mounting plates 1, 3.

Figure 4:
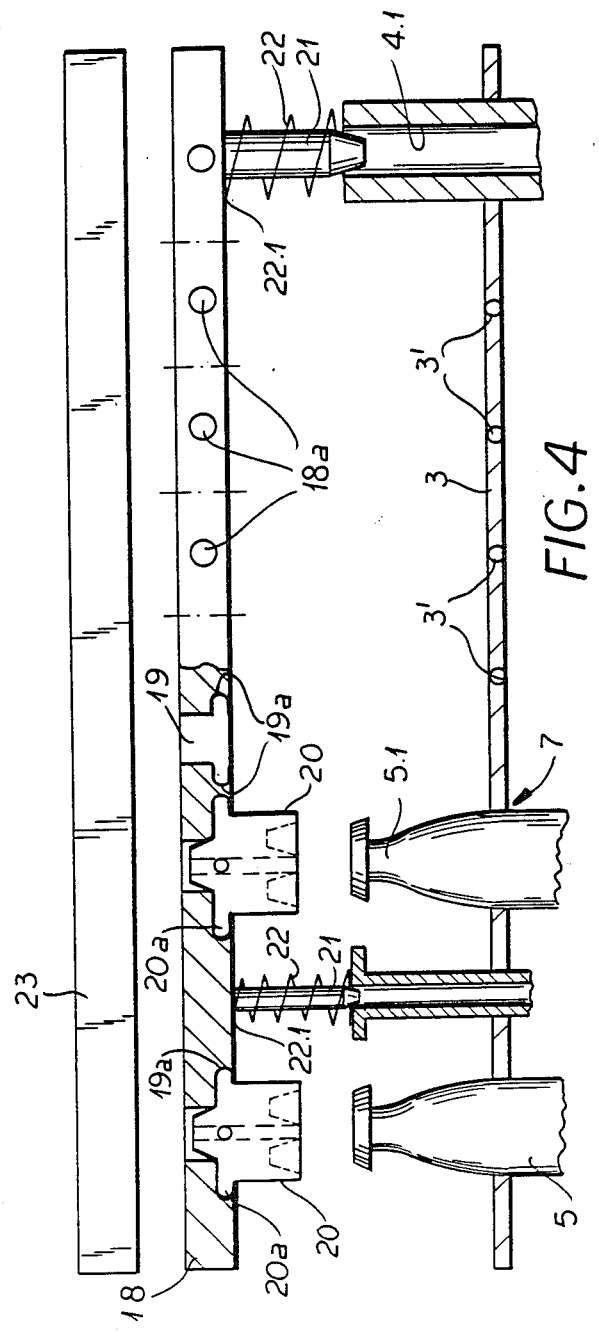
FIG. 4 is a partial cross sectional view corresponding to FIG. 3 with the apparatus upside down and with a closure plate mounted thereon.

The foot members 4 are as seen from FIG. 4 provided with axially extending guiding surfaces 4.1 for a closure member plate 18 movable against the mounting plate 3 and mountable on the mounting plate 3 in a parallel orientation. The closure member plate 18 has mounting sockets 19 for closure members 20 which are positioned again coaxial to the receiving openings 7 in the mounting plate 3. Thus the closure member plate 18 equipped with closure members 20 (adapted to receive the syringe needles) for the furnished syringe bodies 5 allows collectively the furnished syringe bodies 5 at the front piece 5.1 for the ducts to be closed by a single stroke motion toward the mounting plate 3.

The guiding surfaces 4.1 are formed by the cylindrical inner surfaces of the tubular pieces forming the foot members 4 in which guide pins 21 projecting perpendicularly from the closure member plate 18 are guided axially slidably. To make penetration of the guide pins 21 into the guiding surfaces 4.1 of the foot members 4 easier their front ends have a truncated cone shape.

To hold the closure member plate 18 a distance from the mounting plate 3 required for the individual process steps a coil spring 22 is mounted coaxial to each of the guide pins 21 which with its one end 22.1 contacts on the closure member plate 18 and whose other end contacts the front side of the foot members 4. Thus the furnished syringe bodies 5 are freely accessible from both sides and are after shut off of their operation or treatment closed by the closure members 20, the closure member plate 18 being pressed downwardly against the pressure of the spring 22 for example by a press plate 23 which is only indicated in FIG. 4. After the closure members 20 are locked in on the outer mouth edge or lip of the front piece 5.1, the closure member plate 1 is raised again by the spring pressure after unloading by the pressure plate 23 and the locked in closure members 20 remain in the furnished syringe bodies 5.

Since the closure members 20 commonly are afflicted with manufacturing tolerances the danger exists that the closure members 20 can fall out of their mounting openings 19. Thus the mounting receptacles 19 are provided with a circular groove 19a (FIG. 4) in their inner cylinder surface surrounding the closure members 20 in which the closure members 20 engage with radially projecting deformable nap like projections 20a. Because of that the closure members 20 can not be accidentally dislodged from the mounting receptacles 19 although the projections can be readily pulled out from the mounting receiving openings after attachment to the furnished syringe bodies 5.

The supporting plate 1, the mounting plate 3, the retaining plate 11 and the closure member plate 18 are provided in a way not shown in detail with flow passages 1a, 3', 11', and 18a respectively for example in the form of circular ducts to attain a circulating flow during sterilization of the furnished syringe bodies 5 with steam.

To be able to use the apparatus in the temperature range required by the process steps between 350° C. for sterilization and −100° C. for freeze-drying all its parts are made from a form-stable material such as stainless steel.

We claim:

1. An apparatus for handling a plurality of finished syringe bodies comprising:
   a planar supporting plate,
   a mounting plate provided with a plurality of foot members and connected with said supporting plate, said mounting plate being positioned substantially parallel to said supporting plate by a plurality of spacing pieces, both said supporting plate and said mounting plate being provided with a plurality of receiving openings for said finished syringe bodies which traverse coaxial openings in the plates pairwise; and
   a retaining plate provided with a plurality of holes coaxial to and registering with said receiving openings and attachable detachably to said supporting plate on a side of said supporting plate facing away from said mounting plate, the boundaries of said holes in said retaining plate forming an axial contacting surface for said finished syringe bodies placed in said receiving openings, each of said receiving openings being a circular hole, said receiving openings in said supporting plate having a size allowing the receipt of a finished syringe body provided with a bypass, said retaining plate being provided on each of two opposing edges with a respective U-shape profile extending in a longitudinal direction of said edges, wherein both of said grooves formed by said U-shape profiles are open toward one another and form guiding recesses for edges of said supporting plate.

2. The apparatus according to claim 1 wherein said receiving openings are positioned at the insection points of two sets of parallel straight lines positioned equidistantly from each other, said sets of straight lines intersecting each other at an angle of 60°, said straight lines of one of said sets being parallel to a longitudinal side of at least one of said supporting and mounting plate.

3. The apparatus according to claim 1 wherein a free leg of one of said U-shape profiles has a projection protruding in the plane of said leg at the free end of said free leg which forms a contacting surface for one of said spacing pieces with concentric alignment of said receiving openings in said retaining plate and said supporting plate.

4. The apparatus according to claim 3 wherein a retaining pin is positioned on said free leg of said U-shape profile to project into a locking receptacle of said supporting plate with concentric alignment of said receiving openings in said retaining plate and said supporting plate.

5. The apparatus according to claim 4 wherein each of said spacing pieces is formed by a plurality of tubular cylindrical sections and in one piece with one of said foot members.

6. An apparatus for handling a plurality of finished syringe bodies comprising:
   a planar supporting plate,
   a mounting plate provided with a plurality of foot members and connected with said supporting plate, said mounting plate being positioned substantially parallel to said supporting plate by a plurality of spacing pieces, both said supporting plate and said mounting plate being provided with a plurality of receiving openings for said finished syringe bodies which traverse coaxial openings in the plates pairwise; and
   a retaining plate provided with a plurality of holes coaxial to and registering with said receiving openings and attachable detachably to said supporting plate on a side of said supporting plate facing away from said mounting plate, the boundaries of said holes in said retaining plate forming an axial contacting surface for said finished syringe bodies placed in said receiving openings, at least one of said supporting plate, said mounting plate, said retaining plate, and said closure member being provided with a plurality of sterilization-promoting flow passages.

7. The apparatus according to claim 1 wherein said supporting plate, mounting plate, retaining plate, and closure member and said spacing pieces and said foot members are made from a material which is form-stable in a temperature range from −100° C. to 350° C.

8. The apparatus according to claim 7 wherein said material which is nondeformable in said temperature range is stainless steel.

9. An apparatus for handling a plurality of finished syringe bodies comprising:
   a planar supporting plate;
   an mounting plate attached to said supporting plate by a plurality of spacing pieces so that said supporting plate is substantially parallel to said mounting plate and said mounting plate is provided with a plurality of foot members, said mounting plate being provided with a plurality of receiving openings for said furnished syringe bodies positioned pairwise coaxial to each other;
   a retaining plate provided with a plurality of holes coaxial to said receiving openings and connected detachably to said supporting plate on the side facing away from said mounting plate, the boundaries of said holes in said retaining plate forming an axial contacting surface for said finished syringe bodies in said receiving openings, said spacing pieces being divided transverse to the axes thereof and being releasably attached with each other each by a socket sleeve and a socket foot insertable in said socket sleeve, the end of said socket foot carrying an eccentric disk mounted eccentrically on the axis of said socket foot which is found in the extended generated surfaces of said socket foot depending on the rotational position of said eccentric or projectes beyond said socket foot radially and engages in an inner circular groove provided in said spacing piece;

a closure member plate movable toward said mounting plate and mountable in a parallel orientation on said mounting plate, said closure member plate having a plurality of mounting sockets for said closure members which are positioned coaxial to said receiving openings in said mounting plate, said foot members being provided with an axially extending guiding surfaces for said closure member plate which are cylindrical inner surfaces of tubular pieces forming said foot members in which a plurality of guide pins protruding vertically from said closure member plate are guided axially slidably, the front ends of said guide pins being truncated cone shaped and a coil spring being mounted coaxial to each of said guide pins bearing on one end on said closure member plate and on the other end on the front end of said foot member; and a plurality of positioning devices in the form of a plurality of grooves, toothed bars or recesses are provided on said supporting and/or mounting plates for automatic manipulation.

* * * * *